United States Patent

McGregor et al.

[11] 3,976,644
[45] Aug. 24, 1976

[54] METHOD FOR PREPARING 2,5-DIHALOPYRAZINES

[75] Inventors: Stanley D. McGregor; Herman O. Senkbeil, both of Midland, Mich.

[73] Assignee: The Dow Chemical Company, Midland, Mich.

[22] Filed: Dec. 27, 1974

[21] Appl. No.: 537,056

[52] U.S. Cl. .............................................. 260/250 B
[51] Int. Cl.$^2$ ........................................ C07D 241/46
[58] Field of Search ................................. 260/250 B

[56] References Cited
OTHER PUBLICATIONS

Allison et al., J. Chem. Soc. (c), 1970, pp. 1023–1029.

*Primary Examiner*—Paul M. Coughlan, Jr.
*Assistant Examiner*—D. B. Springer
*Attorney, Agent, or Firm*—S. Preston Jones

[57] ABSTRACT

A method for preparing 2,5-dihalopyrazines corresponding to the formula

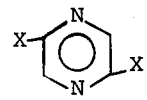

wherein X represents chloro, bromo or fluoro which comprises, reacting a 3,5,6-trihalo-2-hydrazinopyrazine of the formula

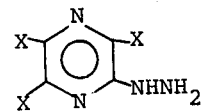

with an aqueous alkali metal hydroxide in the presence of a hydroxylic reaction medium.

3 Claims, No Drawings

METHOD FOR PREPARING 2,5-DIHALOPYRAZINES

BACKGROUND OF THE INVENTION

Dihalopyrazine and especially 2,5-dihalopyrazines are well known materials useful as nitrification inhibitors, and as intermediates in the preparation of insecticides, artificial fibers, detergents and ionic resins as taught in U.S. Pat. Nos. 2,524,431; 2,573,268 and Japanese Pat. No. 17,605/1966.

These compounds can be prepared by a variety of methods including vapor phase halogenation at elevated temperatures with or without the presence of a catalyst and reactions of 3-chloropyrazine-1-oxide with phosphoroyl chloride. Other methods of preparation are continually being sought.

SUMMARY OF THE INVENTION

It has now been found that 2,5-dihalopyrazines corresponding to the formula

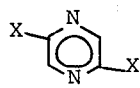

wherein X represents chloro, bromo or fluoro can be prepared in a process which comprises reacting a 3,5,6-trihalo-2-hydrazinopyrazine with an aqueous alkali metal hydroxide in the presence of a hydroxylic reaction medium.

The term "halo" as employed in the present specification and claims designates chloro, bromo and fluoro.

The method of preparation of the present invention can be exemplified by the following reaction scheme:

Reaction Scheme A

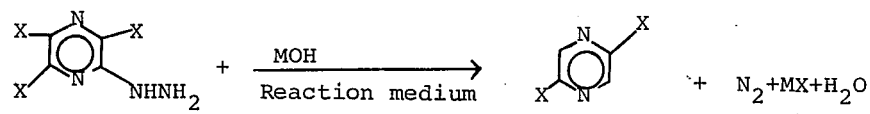

In the above reaction scheme, X is as hereinbefore set forth and M is sodium, potassium, lithium, cesium or rubidium.

Representative 2,5-dihalopyrazines which can be prepared by the method of the present invention are 2,5-dichloropyrazine, 2,5-dibromopyrazine and 2,5-difluoropyrazine.

In carrying out the above reaction, the 3,5,6-trihalo-2-hydrazinopyrazine reactant is mixed with the hydroxylic reaction medium and aqueous alkali metal hydroxide in any suitable fashion and in any order. For example, the pyrazine reactant can be first admixed with the reaction medium and this mixture slowly added to the aqueous alkali metal hydroxide or, the pyrazine reactant can be first admixed with the aqueous alkali metal hydroxide and this mixture added to the reaction medium. The mixture is thereafter held at a temperature of from about 100°C up to the reflux temperature of the mixture until the reaction is complete. The reaction is usually complete in from about 15 minutes to about 1 hour depending upon the specific halopyrazine reactant being employed. Upon completion of the reaction, the reaction mixture is cooled, diluted with water and the crude product removed by solvent extraction with a solvent such as methylene chloride, chloroform, benzene or hexane. The solvent is thereafter removed from the solvent-crude product mixture, with or without additional water washing. The product, if desired, can be further purified by conventional techniques including sublimation, distillation or solvent recrystallization.

Representative trihalo-2-hydrazinopyrazines which may be employed in the practice of the method of the present invention are 3,5,6-trichloro-2-hydrazinopyrazine, 3,5,6-tribromo-2-hydrazinopyrazine and 3,5,6-trifluoro-2-hydrazinopyrazine.

Representative hydroxylic reaction mixture mediums for carrying out the reaction include the hydroxylic solvents boiling above about 100°C including among others for example, the lower alkyl ethers of diethylene glycol, ethylene glycol, propylene glycol, dipropylene glycol and tripropylene glycol and the loweralkyl glycols such as, for example, ethylene glycol, propylene glycol and butylene glycol.

The amount of reactants employed to carry out the reaction is not critical as some of the product will be formed when employing any proportions. The reaction consumes the reactants, however, in the ratio of one molar equivalent of the alkali metal hydroxide per molar equivalent of the trihalo-2-hydrazinopyrazine. It is preferred, however, to employ a slight excess (10-50 percent) of the alkali metal hydroxide to ensure the complete reaction of the 3,5,6-trihalo-2-hydrazinopyrazine reactant.

DESCRIPTION OF SOME PREFERRED EMBODIMENTS

The following examples illustrate the present invention and the manner by which it can be practiced but, as such, should not be construed as limitations upon the overall scope of the same.

EXAMPLE I

2,5-Dichloropyrazine Preparation

A solution was prepared by dissolving 31.7 grams (0.15 mole) of 3,5,6-trichloro-2-hydrazinopyrazine in 150 milliliters of ethylene glycol. The solution was heated to 150°C and a solution of 9.6 grams (0.17 mole) of potassium hydroxide in 50 milliliters of ethylene glycol was added dropwise over 20 minutes and the mixture heated for an additional hour at 150°C. The reaction mixture was cooled, poured into 500 milliliters of water and extracted with methylene chloride. The methylene chloride was removed from the extract by evaporation under reduced pressure leaving ~10 grams of crude 2,5-dichloropyrazine (a brown-red oil) as a residue. The residue was vacuum distilled and 2.75 grams (12.7 percent of theoretical) of a clear oil boiling at 80° at 15 millimeters of mercury was recovered. Analysis confirmed this oil to be the desired isomerically pure 2,5-dichloropyrazine.

By following the above procedures, and employing the appropriate 3,5,6-trihalo-2-hydrazinopyrazine starting material, the following compounds are prepared.

2,5-dibromopyrazine and 2,5-difluoropyrazine.

PREPARATION OF STARTING MATERIALS

The 3,5,6-trihalo-2-hydrazinopyrazines can be prepared by the reaction of an appropriate tetrahalopyrazine with hydrazine hydrate in the presence of ethanol. Such procedure can be found in Allison et al, J. Chem. Soc.(C), 1970 pages 1023–29. A specific preparation is as follows:

3,5,6-trichloro-2-hydrazinopyrazine

A solution was prepared by dissolving 21.8 grams of tetrachloropyrazine in 100 milliliters of dioxane. The solution was diluted with 250 milliliters of ethanol and 15 milliliters of hydrazine hydrate was slowly added thereto. The temperature rose from 23°C to 37°C. The solution was held, with stirring, at 23°C for 20 minutes and the 3,5,6-trichloro-2-hydrazinopyrazine product was isolated by pouring the reaction mixture in water and filtering off the solid product. The product melted at 167°–168°C and was recovered in a yield of 20.2 grams (94 percent of theoretical).

What is claimed is:

1. A method for preparing 2,5-dihalopyrazines corresponding to the formula

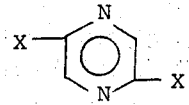

wherein each X represents chloro, bromo or fluoro which comprises reacting at a temperature of from about 100°C. up to the reflux temperature a 3,5,6-trihalo-2-hydrazinopyrazine of the formula

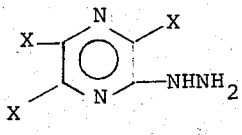

with an aqueous alkali metal hydroxide in the presence of a hydroxylic reaction medium which boils above 100°C.

2. The method of claim 1 wherein the aqueous alkali metal hydroxide is potassium hydroxide and the reaction medium is ethylene glycol.

3. The method of claim 1 wherein the 3,5,6-trihalo-2-hydrazinopyrazine is 3,5,6-trichloro-2-hydrazinopyrazine and the 2,5-dihalopyrazine prepared is 2,5-dichloropyrazine.

* * * * *